United States Patent [19]

Reid

[11] 4,054,050
[45] Oct. 18, 1977

[54] APPARATUS FOR MEASURING THE CRUSH STRENGTH OF SOLID PARTICLES

[76] Inventor: Luther J. Reid, 196 Bishops Drive, Aston, Pa. 19014

[21] Appl. No.: 691,893

[22] Filed: June 1, 1976

[51] Int. Cl.² .............................................. G01N 3/14
[52] U.S. Cl. ...................................................... 73/94
[58] Field of Search .................... 73/94; 177/197, 246, 177/247, 248, 250

[56] References Cited

U.S. PATENT DOCUMENTS

| 2,703,492 | 3/1955 | Brissette et al. ...................... 73/94 |
| 3,580,060 | 5/1971 | Huskey ............................... 73/94 X |
| 3,610,034 | 10/1971 | Gunn et al. ........................... 73/94 |

Primary Examiner—Jerry W. Myracle

[57] ABSTRACT

An apparatus for accurately measuring the force required to crush pellets of solid material. A continuously increasing and accurately known crushing force is applied to the test particle by means of rolling cylindrical metal mass of precisely known weight.

3 Claims, 2 Drawing Figures

APPARATUS FOR MEASURING THE CRUSH STRENGTH OF SOLID PARTICLES

BACKGROUND OF THE INVENTION

1. Field of the Invention

This invention relates in general to the construction of an apparatus for accurately measuring the force required to crush particles of solid material such as contact catalysts, adsorbents, and other particulate solid material. In particular it relates to a new and useful construction for a machine operating on the law of levers whereby a rolling weight applies a gradually increasing and measurable and controlled crushing force to a solid particle.

2. Description of Prior Art

Devices for the measurement of the force required to crush solid particles are widely used in industrial laboratories. Such measurements are called crush tests. The maximum force produced by a dead weight load that a particle can support without losing its integrity is called its crush strength. The figure is useful in predicting whether solid particles arranged in a fixed bed reactor or adsorber will collapse and attrit to a powder during use.

Several methods and devices are available for measuring particle crush strength. In some, a particle is placed between a base and a piston driven from a hydraulic cylinder. Fluid pressure in the cylinder is increased until the particle collapses. Its crush strength is measured from the known cylinder pressure and total force on the piston caused by that pressure. Air or water or oil have been used as the pressurizing fluid in such devices.

In another type of device a spring force is used instead of hydraulic force. An anvil is pressed against the particle by means of a spring. The force on the particle at the instant it collapses is measured and computed from the measured spring length at the instant of particle collapse.

In most available methods the particle can be placed on a base and the crushing force applied vertically downward, or the particle can be pushed against a retaining wall and the force applied laterally.

Disadvantages of the commercially applied methods are the inaccuracies introduced by such things as erroneous or inoperative pressure gauges, errors in knowing the correct value of the spring constant or even having a spring in the apparatus which is different from the one that is thought to be there. Furthermore, different calibration curves are needed from time to time to convert spring elongations or pressure guage readings into crushing force. Unless special means are incorporated into such devices, the rate at which load is applied to the particle is generally not known even though such rate of application has a profound effect on the ultimate crush strength of the particle.

A very crude particle crush tester is a hand nutcracker of the type where the nut to be cracked is placed between two hinged members. The members are then squeezed together by hand to crack the nut. The problem with this type of crush tester is that measurement of crush strength is inaccurate since it depends on the personal judgement as to what position along the members it was held, where the nut was actually located and how hard and how fast it was squeezed. In the subject invention a way has been discovered to simply quantify such a nutcracker principle and thereby produce a very simple and vastly superior crush strength tester.

DESCRIPTION OF THE INVENTION

The invention provides a way to measure the crush strength of solid particles gravimetrically by using precisely known weights, the lever law, and the construction of the subject invention to apply a continuously increasing and accurately known crushing force to a solid particle. More particularly, the invention comprises the combination of a hinged beam and stationary base, two opposing anvils, one of which is attached to the beam and which contacts one side of the particle to be crushed; the other anvil supports the particle in place from the approximately opposite side; and there is a means for applying a continuously increasing crushing force to the particle through the anvil attached to the beam. The preferred means of applying the continuously increasing crushing force to the particle is by rolling a cylindrical metal mass of precisely known weight along the beam from the fulcurm to the far end.

The preferred embodiment of the invention may be described further by the way it works. A particle to be tested is placed between anvils attached to the hinged beam and base. The beam, a channel with flat top and side flanges, has a meter scale attached on a side flange that measures the distance from the hinge, which is the fulcrum, and the free end of the beam. The apparatus is adjusted so that the beam resting on the particle slopes downward from the fulcrum. A rollable cylindrical metal load mass of known weight, typically about 2 kilograms, is placed over the fulcrum and released to roll or is pushed along. As it rolls slowly down the flat top of the beam its position is continually noted with respect to the beam scale. When the particle collapses the beam drops and the position of the weight is noted at that instant. The crush strength of the particle is computed by the relationship $$C = (S/D) \cdot W$$

Where
C = crush strength in units of W
W = weight of load on beam
S = distance of W from fulcrum at instant of particle collapse
D = distance of crushed particle from the fulcrum in same units as S.

The invention may be described more fully by examing a particular embodiment in the Drawings.

Figure 1:
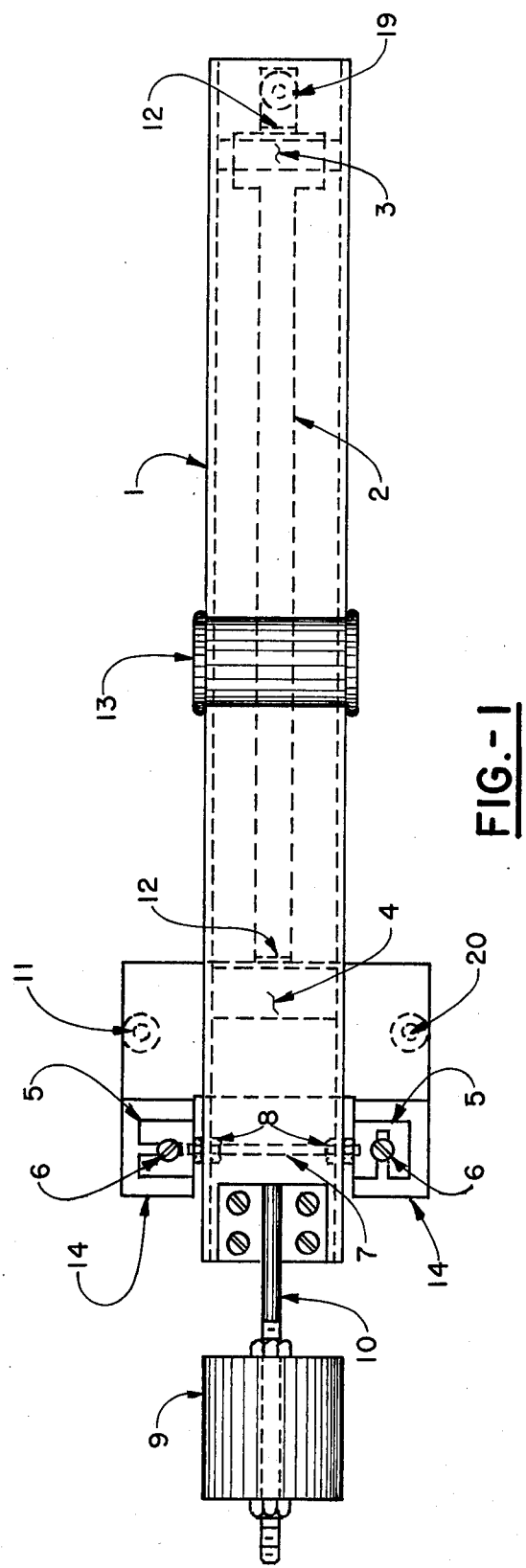
FIG. 1 shows a top view of the apparatus without the solid particle to be tested.

Referring to FIG. 1, the apparatus comprises beam 1 connected to the base 2 by means of pin 7. Pin 7 is clamped to beam 1 by nuts 8 and is supported by the two supports 5 at each end. The assembly of parts 7, 8 and 5 as shown in both a hinge and a fulcrum for the beam 1. The beam 1 is attached to counterweight 9 through connecting member 10 to form the counterbalanced beam assembly comprising parts 1, 9 and 10. The weight of 9 and length of 10 are selected and adjusted so that the beam is balanced in a level position when supported only by fulcrum 7. Machine screws 6 fix the supports 5 to the base so that the supports do not move as the beam is raised or lowered or as the rollable load mass rolls or is rolled along the beam.

Figure 2:
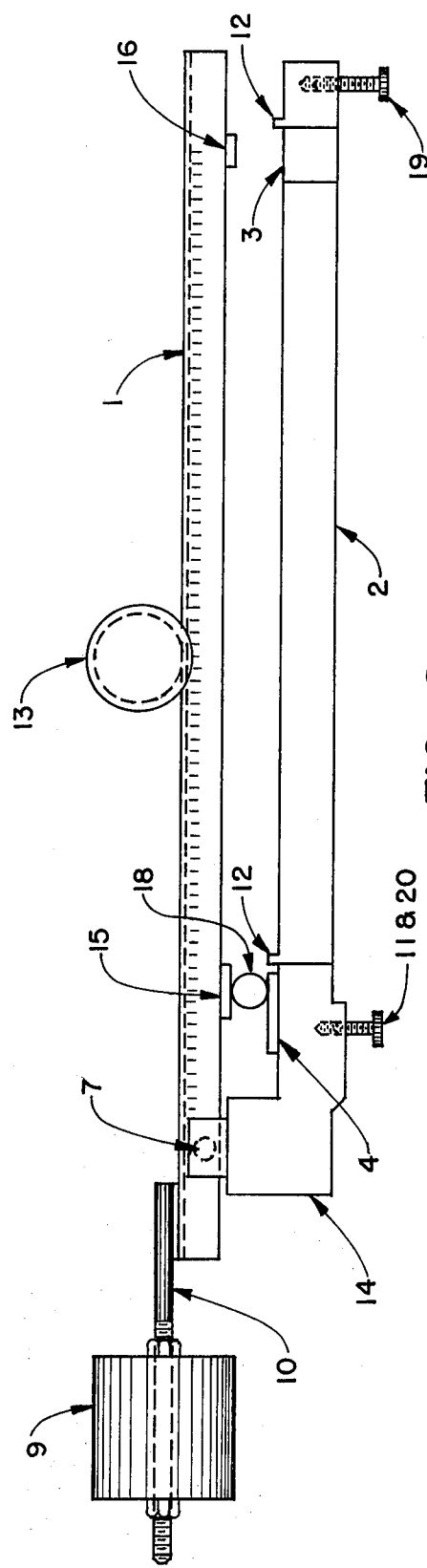
FIG. 2 is an elevation view of the apparatus of FIG. 1 and includes also a solid spherical particle in place for testing on the rear anvil and a metal spool sitting on the beam.

Referring to FIG. 2, anvils 15 and 16 are the top crushing anvils and are attached to the beam over base positions at 4 and 3 respectively. Solid particles are tested by crushing them at either the 4 or 3 position depending on the amount of force required. Anvil 4 is a movable bottom anvil placed on the base 2 at either position 4 or 3. Anvil 4 serves to support the catalyst in place as it is crushed. The ridges 12 are stops that aid in positioning the anvil at either the forward 3 or rear 4 location.

Solid particle 18 is shown positioned between the two anvils 15 and 4. The thickness of avil 4 is selected such that when top anvil 15 is in contact with the particle there is a clearance of about 1/16 inch or more between anvil number 16 and the base; also the beam 1 is approximately level and may be sloping slightly downward from the fulcrum. The slightly sloping beam helps the load to roll smoothly down the beam.

Load 13 is a metal rollable spool of known weight that can be rolled along the beam.

The three feet 11, 19 and 20 are independently adjustable for the purpose of adjusting the apparatus so that the rollable mass 13 when placed on beam 1 over the fulcrum, slowly and freely rolls to the free end.

The rear of the base is a two pronged fork with ends shown as 14. The rear feet 11 and 20 rest on the end of a table or support so that the prongs of the fork extend beyond the edge of the support. Such arrangement permits connecting number 10 and counterweight 9 to swing down through the prongs of the fork as the beam is raised to a vertical position.

For the apparatus shown in FIGS. 1 and 2, beam 1 is an aluminum channel, $3 \times 1 \times 1$ inch size, 45 inches long and weighing 6 pounds. The cylindrical type load rolls along the 3 inch flat surface. Pin 7 is 4 1/16 inch threaded 7/16 inch diameter pin with ends machined smooth to turn in steel $1 \times 1 \times 1$ inch fulcrum supports 5. Connecting member 10 is 22-inch-long ¼ inch threaded steel rod. Counterweight 9 is 5.5 pounds of cylindrical cast iron 3.0 inches in diameter. Base 2 is cast iron, 46 inches in overall length, 7 inches wide at the rear fork, and weighs 22 pounds. Overall height with the beam in a horizontal position is about 4.5 inches. Adjustable feet can raise and lower the rear anvil position about 1 inch. Anvils attached to the beam are $3 \times 1 \times \frac{1}{4}$ inch hardened steel which are bolted to a support member welded to the beam flanges. The anvil that rests on the base is $2 \times 2 \times \frac{1}{4}$ inch hardened steel. Pin 7 and supports 5 may be hardened steel to impart longer life to those parts. The rollable load mass is a cylinder mass two inches in diameter 2 kilogram brass machined to give a smooth rolling surface. The scale attached to the side of the beam is 100 centimeters long. The rear anvil position is located to crush particles 10 centimeters from the fulcrum. The forward anvil position is for placing particles 100 centimeters from the fulcrum.

Operation is as follows for the case where it is desired to test hard particles. Because particles are hard, the rear position 4 is selected for testing because greater force due to greater leverage of the rollable weight on the beam are generated there. The rolling weight 13 is removed from beam 1 by simply lifting it off and setting it down somewhere else. Beam 1 is lifted to a vertical position. The rear anvil 4 is positioned against the rear stop on the base. A solid particle 18 is placed on anvil 4. Beam 1 is gently lowered until anvil 15 contacts particle 18. The position of particle 18 on the beam scale is noted for the crush strength computation.

The particle 18 is said to be clamped in place when it is in contact with both the bottom and top anvils even though the force on the particle caused by resting the counterbalanced beam on the particle is essentially zero.

The feet 11, 20, and 19 are adjusted so that the beam is level or sloping away from the fulcrum. The rollable load mass of known weight is placed on the beam over the fulcrum 7 and given a gentle push to cause it to roll along the beam. The position of the rolling load is noted when the particle collapses causing the beam to drop. The crush strength may then be computed.

A suitable sample of catalyst or adsorbent consists of many particles and contains particles having wide variations in crush strengths. It is therefore desirable to test many particles to obtain an average crush strength value representative of the sample. The subject invention permits such rapid testing.

In other embodiments of this invention a suitable beam may have other configurations. For example, a flat beam with narrow edge up can be used, but in this case it is necessary to use a rolling mass unlike any described previously. For a narrow edge beam a grooved pulley wheel rolling along the thin edge, with attached and suspended weight, may be rolled along the beam to vary the load on the solid particle. For measuring very high or very low crush strengths apparatus of different size, material, and configuration may be used.

The fulcrum bears a downward force when the rolling load mass is between the fulcrum and the catalyst particle, an upward force when it is at other positions. Therefore, if only a forward or only a rear anvil position is needed the fulcrum may be an appropriate knife edge bearing with hinging that accomodates only upward or only downward force at the fulcrum. Preferably the fulcrum is a pin, like pin 7 of FIG. 2, and the beam can rotate through an angle of at least 90°.

If a high and low range of crush strengths is to be tested on the same machine the fulcrum should be confined from both top and bottom directions. In the preferred embodiment the hinge and the fulcrum are the same thing and are so confined. It is an essential feature of the invention that the beam rotatable or removable in order to move it out of the way while a solid particle is placed on the anvil for testing. When a knife edge fulcrum is used the beam is most conveniently made readily and quickly removable from the base, even though such a beam is considered to be hinged in the practice of this invention.

The counterweight is needed in order for continuous crush strength values of 0 to the maxium to be measurable. It may be screwed, bolted, or welded to the beam or to a connecting member. A long symmetrical beam with fulcrum at the center of gravity is a case where one half the beam provides the counterweight.

A base of heavy cast iron will not move out of position as the beam is raised and lowered. Other fabricated forms are suitable as long as the fulcrum can be attached or incorporated and bottom anvil can be provided.

The practice of this invention depends on having an anvil, usually a bottom anvil, positioned directly opposite the beam anvil when the beam is in a horizontal position. The bottom anvil may be simply a flat place on the base but is preferably a piece of hardened steel that can rest flat on the base or is attached to it. An advantage of a separate steel anvil is that the distance between beam anvil near the fulcrum and bottom anvil can be adjusted to give best crushing results by adjusting the thickness of the bottom anvil.

Any bottom anvil position or any number of them may be used, and their locations are measured against the beam scale. For convenience, and to minimize beam weight thereby increasing sensitivity, a typical construction provides only a rear anvil position 10 centimeters from the fulcrum and a forward anvil position 100 centimeters from the fulcrum. The rear position is convenient for testing particle crush strengths over 2 kilograms and the forward position for testing under 5 kilograms. A single anvil that traverses the length of the beam or base may be used. Such would be the case where a steel bar serves as both beam and beam anvil.

An essential feature of the subject invention is the means for continuously increasing the crushing force on a particle clamped between the anvils. The preferred method is to provide a rigid solid mass that moves or is moved along the beam to provide a gradually increasing downward force on the solid particle. A cylindrical solid rigid block of metal, machined to a uniform diameter, is especially suitable because the center of gravity of such a piece does not change as it rolls along the beam and therefore movement is especially smooth. Satisfactory rollable masses may also be cast, machined or otherwise shaped as spools which are cylinders with concentric circular flanges on the end and which roll either on the flanges, or preferably, on the cylindrical section between them. Other shapes that have a cylindrical section to roll on the beam are also suitable. For broad flat top beams a small 3 or 4 wheel cart loaded with weight such as steel, lead shot or slugs may be used as a rollable mass.

Sliding masses may be used with other special means for moving them parallel to the beam surface. The rollable rolling mass provides a less expensive and more rapid method of applying a continuously and slowly increasing load to the particle and is therefore preferred.

Although the movable mass preferably is solid, rigid metal such as brass, aluminum, cast iron or stainless steel, it may also be a rigid cylindrical closed can filled with a fluid such as mercury or particles such as lead shot. Movable masses suitable for loading the beam typically lie in the range of 500 grams to 5 kilograms.

In still another embodiment the top of the beam may be two parallel rods or beam edges and the movable mass a metal sphere of greater diameter than the distance between such rods.

Another means of applying a continuously increasing crushing force is to suspend or sit a container on or near the free end of the beam and slowly discharge into it a stream of water or some other liquid. Because the fluid discharge is continuous and is usually at a constant rate, the crushing strength on the particle increases gradually, depending on flow rate, and continuously. An alternate method that produces a load increase that can be considered continuous is the discharge of a stream of lead or steel shot into the container. However, the rollable rigid mass, rolling along the beam provides a simple, rapid and clean method for applying a continuously increasing crushing strength.

The applied crushing strength may be an upward or downward force depending on the apparatus configuration. In designs where the particle is crushed on the opposite side of the fulcrum from the applied beam load, the crushing force is upward and a rigid top anvil above the beam anvil must be provided to retain the particle.

The beam scale marked off along the side, as shown in FIG. 2, or top of the beam to measure distance from the fulcrum may be in any uniform and constant units. A centimeter scale marked in half-centimeters is preferred.

The meter scale gives good accuracy because of its length, equivalent to a dial scale of 12 inches in diameter.

Particles tested for crush strength by the subject invention are typically in the range of 1/16 to ½ inches in diameter and may be tablets or extrudates of various lengths, or beads or irregular granules within this size range. Generally, particles with a minimum width or diameter greater than 1/32 inches can be tested with the subject invention.

In the practice of this invention the use of a wide beam is far superior to other types.

In the preferred embodiment of this invention the beam is wider than it is deep. When the beam is wide it is better positioned by the fulcrum and the rolling mass can be small enough in diameter to be readily manipulated manually even when crush strengths as high as 150 pounds are being measured. A wide channel beam, with flat top up, provides a surface that small masses can be rolled on without the inconvenience of having them roll off the beam before they traverse the full distance from fulcrum to end. For best operation the width of the beam should be not less than one inch and preferably is two to four inches. Because the beam must be not only wide but also should be light in weight the preferred embodiment of this invention includes a beam that is wider than it is deep. Thus a 1×1×3 inch or ½×½×1 inch channel beam or a 1×2 inch angle beam or a solid ½×2 inch flat bar are all wider than deep when the widest surface is used as the rolling surface as is the case in the preferred embodiment of this invention.

I claim:

1. In an apparatus for measuring the crush strength of a solid particle the combination of a counter-weighted beam hinged to a stationary base said beam being wider than it is deep, two anvils for clamping said particle between them, one of said anvils attached to said beam for applying force to said particle and other of said anvils for supporting said particle in place and a rigid rollable metal mass movable along said beam to provide an increasing crushing force to said solid particle.

2. The combination of claim 1 wherein the anvil for supporting the particle in place is movable.

3. The combination of claim 2 wherein the beam is marked with a scale for measuring the position of the rollable metal mass.

* * * * *